US007728184B2

(12) United States Patent
Lucchini et al.

(10) Patent No.: US 7,728,184 B2
(45) Date of Patent: Jun. 1, 2010

(54) PROCESS FOR THE DEHYDROGENATION OF ALKYL-AROMATIC HYDROCARBONS FOR THE PRODUCTION OF VINYL-AROMATIC MONOMERS

(75) Inventors: Mario Lucchini, Curtatone-Mantova (IT); Armando Galeotti, Gonzaga-Mantova (IT)

(73) Assignee: Polimeri Europa S.p.A., San Donalto Milanese (IT)

( * ) Notice: Subject to any disclaimer, the term of this patent is extended or adjusted under 35 U.S.C. 154(b) by 148 days.

(21) Appl. No.: 12/159,162

(22) PCT Filed: Dec. 18, 2006

(86) PCT No.: PCT/EP2006/012325

§ 371 (c)(1),
(2), (4) Date: Jun. 25, 2008

(87) PCT Pub. No.: WO2007/073918

PCT Pub. Date: Jul. 5, 2007

(65) Prior Publication Data

US 2009/0043142 A1   Feb. 12, 2009

(30) Foreign Application Priority Data

Dec. 29, 2005  (IT)  .......................... MI2005A2514

(51) Int. Cl.
*C07C 5/327* (2006.01)
*C07C 2/64* (2006.01)

(52) U.S. Cl. ........................ 585/323; 585/441; 585/440; 585/446; 585/950

(58) Field of Classification Search ................. 585/323, 585/441, 440, 446, 950
See application file for complete search history.

(56) References Cited

U.S. PATENT DOCUMENTS

| 3,690,839 | A | | 9/1972 | Jones |
| 4,009,217 | A | * | 2/1977 | Uitti .......................... 585/323 |
| 4,615,769 | A | | 10/1986 | Horigome et al. |
| 5,856,605 | A | | 1/1999 | Deimling et al. |
| 6,171,449 | B1 | | 1/2001 | Welch |

\* cited by examiner

*Primary Examiner*—Thuan Dinh Dang
(74) *Attorney, Agent, or Firm*—Oblon, Spivak, McClelland, Maier & Neustadt, L.L.P.

(57) ABSTRACT

Process for the production of vinyl-aromatic monomers which comprises: a) feeding an aromatic stream and an olefinic stream to alkylation; b) feeding the reaction product coming from the alkylation section to a first separation section; c) recovering the mono-alkylated aromatic hydrocarbon from the first separation section; d) feeding the mono-alkylated aromatic product to a dehydrogenation section; e) cooling and condensing the reaction gases in the shell of one or more heat exchangers; f) feeding the reaction product coming from the dehydrogenation section to a second separation section; g) recovering the stream of vinyl-aromatic monomer.

15 Claims, No Drawings

PROCESS FOR THE DEHYDROGENATION OF ALKYL-AROMATIC HYDROCARBONS FOR THE PRODUCTION OF VINYL-AROMATIC MONOMERS

The present invention relates to an improved process for the dehydrogenation of alkyl-aromatic hydrocarbons for the production of vinyl-aromatic monomers.

More specifically, the present invention relates to an improved process for the production of vinyl-aromatic monomers coming from the dehydrogenation of the corresponding alkylated products.

Even more specifically, the present invention relates to an improved process for the dehydrogenation of ethyl-benzene for the production of styrene.

Vinyl aromatic monomers, such as styrene, are particularly known for their use in the preparation of plastic materials, such as compact/crystalline polystyrene (homopolymer), compact high impact polystyrene (HIPS), expanded polystyrene and other products. These monomers are prevalently produced starting from the corresponding alkyl-aromatic product which is first dehydrogenated, in gaseous phase, at a high temperature and low pressure, in the presence of steam, on suitable catalysts based on iron and potassium oxides. The effluent coming from the dehydrogenation reaction, which contains various hydrocarbon products formed under the reaction conditions, is first condensed and subsequently sent to a purification section where said effluents in the liquid state are treated to separate and purify the various components by means of a series of fractionation columns operating in series, with respect to the flow of vinyl-aromatic monomer.

In the case of styrene, the process generally envisages feeding ethylbenzene to a device, normally a heat exchanger, where the ethylbenzene is vaporized in the presence of steam; the mixture is sent to a system of heat exchangers where the vapour is overheated and, after mixing with further steam at a high temperature, it is subsequently sent to the first reaction step. At the outlet of the first reaction step, the mixture is heated in a suitable exchanger system, and then sent to the subsequent reaction step, possibly followed by a third. The effluent from the last reaction step is cooled, by preheating the ethylbenzene and the vapour which then feed the reaction section itself.

In some cases, the heat recovery can be effected by generating and overheating the steam alone or vaporizing and overheating an azeotropic mixture of ethylbenzene and water.

At the outlet of the heat recovery section, the reaction mixture undergoes a further cooling, by contact with vaporizing water, and is then condensed in one or more heat exchangers, transferring heat to cooling water or, sometimes, air.

The condensing system typically consists of 2 exchangers in series. The first is that in which most of the condensation takes place, normally inside tubes, and wherein the cooling fluid can be either air or water. The second exchanger, which is smaller, can be installed either in a horizontal or vertical position and is that in which the cooling of the incondensable part takes place, normally inside tubes and in which the cooling fluid is usually water.

A two phases liquid mixture leaves the condenser, which is separated by decanting in an appropriate drum, together with a gaseous phase, rich in hydrogen, which is sucked by suitable compressors and is then sent, after purification in a specific section, for other uses. After separation by gravity, the two liquid phases are suitably treated. The aqueous phase is purified by the residual hydrocarbons and then removed, whereas the hydrocarbon phase is sent to the purification section consisting of fractionation columns, which can be three or four, depending on the type of process.

The liquid mixture of aromatic hydrocarbons coming from the dehydrogenation section is fed into the first column. In this column, a mixture of benzene and toluene is separated at the top, which forms a by-product of the production process of styrene, whereas a stream containing non-reacted ethylbenzene, styrene and high-boiling products is extracted from the bottom. The stream coming from the bottom of the first column is fed to a second column, where a stream containing non-reacted ethylbenzene is separated at the top and recycled to the dehydrogenation section, whereas a stream containing styrene together with high-boiling products is extracted from the bottom. The flow coming from the bottom of the second column is fed to a third column, where the styrene forming the end-product is removed at the top, whereas a stream consisting of styrene and high-boiling products is extracted from the bottom.

As the concentration of styrene present in the stream leaving the bottom of the third purification column is still high, it is further treated in a fourth column, or different apparatus, such as an evaporator. A stream rich in high-boiling products which forms the process residue is produced and removed from the latter part of the purification section, whether it be a distillation column or an evaporator.

What is indicated above is one of the possible production schemes of styrene. There is at least a second scheme, also widely used, which mainly differs in the purification phase. This has a dehydrogenation section completely analogous to that previously described but the purification is based on three columns.

In this case the liquid hydrocarbon mixture is fed to the first column, where a mixture of benzene, toluene and ethyl benzene is separated at the top, whereas a stream containing styrene and high-boiling products is separated at the bottom. The product extracted from the top is fed to a second column where a mixture of benzene and toluene, which forms a by-product of the production process of styrene, is extracted from the top, whereas a stream containing non-reacted ethylbenzene is obtained at the bottom and is sent to the dehydrogenation unit.

The stream coming from the bottom of the first column is fed to the third column, where purified styrene is extracted from the top, whereas a stream whose composition is similar to that described in the previous scheme, is obtained at the bottom, which, as it is still rich in styrene, is further treated to recover this with procedures similar to those described above.

The residue contains significant quantities of heavy, viscous materials consisting of pitches and/or other polymeric products which are formed as a result of the processing process.

There is finally a third scheme for the production of styrene, less frequently applied, which differs with respect to the reaction part. According to this scheme, after the first dehydrogenation reaction step, there is a section in which the effluent from the reactor is heated as a result of an oxidation reaction carried out on a suitable layer of catalyst. Thanks to the catalyst, the oxidation, effected by introducing air or oxygen, does not influence, or only to a minimum extent, the hydrocarbons present but mainly the hydrogen formed after passage in the first dehydrogenation reactor. The reaction mixture leaving said oxidation step, impoverished in hydrogen and having a higher temperature, is fed to the second dehydrogenation step where the ethylbenzene is converted to styrene, under conditions particularly favoured by the absence of the hydrogen formed in the previous step.

Also in this case, there can be a third dehydrogenation step preceded however by a second oxidation step.

The effluent from the last dehydrogenation reactor is cooled and condensed with exactly the same procedure as described above. Analogously, both the liquid and gaseous effluents are in turn treated as specified above.

Regardless of the procedure with which the dehydrogenation is carried out and the method used for the heat recovery of the gases leaving the reactors, the products of the various reactions comprise, in addition to styrene, other chemical substances, some low-boiling, for example methane, ethane and ethylene, which follow the gaseous phase, others such as benzene, toluene, stilbene, divinyl-benzene and other high-boiling products, which condense and form the liquid mixture which is sent to the subsequent purification section. The high-boiling substances formed, some of which, such as stilbene, have high melting points, tend to form small quantities of solid or liquid but extremely viscous particles which have the tendency to become deposited inside the apparatus during the cooling and condensation phase of the effluent from the last dehydrogenation reactor.

In order to overcome this problem, in the production processes of styrene described above, before the condensation phase, there is a cooling phase by direct contact with water. This operation allows most of the fouling particles mentioned above to be removed, preventing them from interfering with the exchangers and machines situated downstream. During this phase of the process, solid or extremely viscous liquid particles do in fact tend to condense on the surface of the drops of water sprayed in the effluent gases and therefore to be removed from the system together with these. A small but significant fraction of high-boiling substances which are formed during the cooling phase of the solid or extremely viscous liquid substances, is not stopped by the water washing and therefore reaches the equipment downstream, where the condensation of the reaction effluent is effected. Part of this fraction is entrained with the gaseous effluent reaching the compressors.

Experience has shown that the presence of small deposits of solid or extremely viscous substances, as described above, can cause serious drawbacks in the functioning of styrene production plants. Once deposited, in fact, for example on the surface of the heat exchanger pipes, their dimensions tend to increase, absorbing styrene together with small quantities of divinyl-benzene directly from the gaseous phase containing them. Once absorbed, the styrene follows its natural tendency to polymerize, thus forming an additional solid mass which consequently increases the small particles of high-boiling substance originally deposited. The low temperature, with respect to those in which the polymerization of styrene normally takes place, and the presence of small quantities of divinyl-benzene, a product which contributes to increasing the molecular weight of the polymer forming reticulations, makes the polymer formed completely insoluble with the result that it is extremely difficult to remove.

The consequences of the deposition and growth phenomenon with time of solid masses inside the condensing system and at times inside the hydrogen compressors create, either totally or partially, a sequence of undesired events as described below:

1. decrease in the thermal exchange efficiency, particularly on the condenser;
2. increase in the condensation pressure and consequently the pressure upstream of the condensing system, in particular inside the dehydrogenation reactors, to compensate the reduced heat exchange efficiency;
3. increase in the condensation pressure and consequently upstream of the condensing system, in particular inside the dehydrogenation reactors, due to the increase in the pressure drops, caused by the decrease in the passage section as a result of the growth of the solid material deposits;
4. lower yield of the dehydrogenation reaction due to the increase in the pressure inside the reactors, caused by both a decrease in the conversion and a decrease in the selectivity.
5. decrease in the plant production capacity caused by: a decrease in the yield, a decrease in the thermal exchange efficiency and a decrease in the passage sections of the gases;
6. production loss due to the necessity of shut down for cleaning, when the phenomena described above make continuation uneconomical;
7. increase in costs, in particular those due to the shut down of the plant and those for the cleaning of the equipment;
8. serious damage to the equipment with the consequent necessity of shut down and substitution of parts thereof, when cleaning is not possible.

The Applicant has now found, as described in the enclosed claims, a condensing system which prevents the occurrence of the undesired phenomena listed above as it is completely free of deposition phenomena of solid materials, according to the mechanism described above.

An object of the present invention therefore relates to an improved process for the production of vinyl-aromatic monomers which comprises:

a) feeding a stream consisting of an aromatic hydrocarbon together with a stream essentially consisting of a $C_2$-$C_3$ olefin to an alkylation section;

b) feeding the reaction product coming from the alkylation section to a first separation section;

c) discharging from the first separation section a first stream consisting of non-reacted aromatic hydrocarbon, which is recycled to the alkylation section, a second stream essentially consisting of a mono-alkylated aromatic hydrocarbon, a third stream essentially consisting of dialkylated aromatic hydrocarbons, sent to a transalkylation section, and a fourth stream essentially consisting of a mixture of polyalkylated aromatic hydrocarbons;

d) feeding the second stream of step (c) to a dehydrogenation section;

e) sending the stream leaving the last dehydrogenation reactor, after a first cooling with heat recovery and a sub-sequent washing with sprayed water, to a section in which the condensation takes place of most of the stream by thermal exchange in specific equipment;

f) feeding the reaction product coming from the condensation section (e) to a second separation/purification section, comprising at least one distillation column;

g) discharging a stream consisting of the vinyl-aromatic monomer with a purity higher than 99.7% by weight from the head of said at least one distillation column.

According to the present invention, the aromatic hydrocarbon fed to the alkylation section can be selected from those with a number of carbon atoms ranging from 6 to 9 but is preferably benzene. Other aromatic hydrocarbons which can be used in the process, object of the present invention, can be selected from, for example, toluene and ethyl-benzene.

The preferred hydrocarbon is refinery-grade benzene with a purity higher than or equal to 95% by weight.

The C$_2$-C$_3$ olefinic stream, for example, ethylene or propylene, also refinery-grade with a purity higher than or equal to 95% by weight is fed to the alkylation reactor together with the aromatic hydrocarbon, fresh and, optionally, recycled. The two aromatic and olefinic streams are fed to the alkylation unit so as to have aromatic/olefin molar ratios which satisfy the requirements of current technologies, typically from 1.8 to 50, preferably from 2 to 10.

The alkylation reaction is carried out with conventional catalytic systems, for example according to the method described in European patent 432,814.

Any alkylation reactor can be used in the process object of the present invention. For example, fixed bed or fluid bed reactors, transport bed reactors, reactors operating with a slurry mixture and catalytic distillation reactors, can be adopted.

The preferred alkylation catalysts can be aluminum trichloride or those selected from synthetic and natural porous crystalline solids based on silicon and aluminum, such as acid zeolites in which the silicon/aluminum atomic ratio ranges from 5/1 to 200/1. In particular, Y, beta, omega zeolites, mordenite, A, X and L and the crystalline porous solids MCM-22, MCM-36, MCM-49, MCM-56 and ERS-10 are preferred. Alternatively, it is possible to use synthetic zeolites of the ZSM group in which the silicon/aluminum atomic ratio ranges from 20/1 to 200/1, such as ZSM-5 zeolite.

The alkylation reaction can be carried out under temperature and pressure conditions which depend, as is well known to experts in the field, not only on the catalyst selected but also on the type of reactor and choice of reagents. In the case of the alkylation of benzene with ethylene, the reaction temperature generally ranges from 100 to 450° C. More specifically, with zeolitic catalysts, for either fixed or mobile bed processes in gas phase, the temperature preferably ranges from 300 to 450° C. or from 180 to 250° C. for processes in liquid phase, whereas in the case of a catalytic distillation reactor, operating in mixed gas-liquid phase, the reaction temperature, varying along the catalytic bed, ranges from 140 to 350° C., preferably from 200 to 300° C. When reactors operating with a slurry mixture and an aluminum trichloride catalyst, are used, the temperature ranges from 100 to 200° C.

The pressure inside the alkylation reactor is maintained at values ranging from 0.3 to 6 MPa, preferably from 0.5 to 4.5 MPa.

The aromatic stream leaving the alkylation reactor is treated with conventional means for recovering the reaction product from the non-converted reagents and reaction byproducts. In particular, the separation system preferably consists of a series of at least three distillation columns from which the non-reacted aromatic compound is recovered from the first, and recycled to the alkylation reactor and/or a transalkylation unit described below. The monoalkyl-substituted aromatic compound, for example ethyl-benzene, is recovered from the second distillation column and fed to the dehydrogenation unit, whereas the dialkylated aromatic products are recovered from the head of the third column and sent to the transalkylation unit, and the heavy products, essentially consisting of polyalkylated products, tetralines and alkyl-substituted diphenyl ethanes, which can be fed as additives to the second separation/purification section of the product coming from the dehydrogenation section, are recovered from the bottom.

The dialkylated aromatic compounds, for example diethyl benzenes, can be fed to a transalkylation reactor for transalkylation with C$_6$-C$_9$ aromatic hydrocarbons, for example benzene, to produce the corresponding mono-alkyl substituted aromatic compounds, such as ethyl-benzene, and increase the yield of the alkylation production.

The transalkylation can take place in a specific reactor or in the same alkylation reactor.

The transalkylation reactor, when present, preferably consists of a reactor operating in slurry phase, when the catalyst is aluminum trichloride, or in a fixed bed reactor, functioning in liquid phase, in which a conventional zeolitic transalkylation catalyst is present, such as Y zeolite, beta zeolite or mordenite, preferably Y or beta zeolite. The transalkylation reaction can be carried out according to what is described in European patent 847,802.

In the case of the transalkylation of diethyl-benzene with benzene, the benzene/ethylene molar ratio, calculated with respect to the total moles of benzene present as such and as diethyl-benzene and the total moles of ethylene pre-sent as substituents in the diethyl-benzenes, ranges from 2/1 to 18/1, preferably from 2.5/1 to 10/1. The temperature in the reactor is maintained at a value of 50 to 350° C., preferably from 130 to 290° C., whereas the pressure is maintained at 0.02 to 6 MPa, preferably from 0.5 to 5 MPa.

The mono-alkylated aromatic product is fed to the catalytic dehydrogenation section which comprises one or more reactors operating with a fixed bed or fluid bed. The dehydrogenation reaction with a fluid bed reactor takes place at a temperature ranging from 450 to 700° C. and at a pressure ranging from 0.01 to 0.3 MPa, in the presence of a catalyst based on one or more metals selected from gallium, chromium, iron, tin, manganese supported on alumina modified with 0.05-5% by weight of silica. In addition to the above metals, the catalytic system can comprise platinum and/or one or more alkaline or alkaline earth metals. Examples of dehydrogenation processes of alkyl-aromatic hydrocarbons are described in Italian patent 1,295,071, in U.S. Pat. Nos. 5,994,258 and 6,031,143 or in international patent applications WO 01/23336 or WO 03/53567.

The dehydrogenation reaction with a fixed bed reactor takes place at a temperature ranging from 500 to 700° C., preferably from 520 to 650° C., at a pressure ranging from 0.02 to 0.15 MPa, in the presence of a catalyst based on iron oxide and potassium carbonate containing other metallic compounds in small quantities having the function of promoters.

In the case of the production process of styrene, the dehydrogenation can take place, for example, with a fixed bed catalyst by feeding a mixture of ethyl-benzene vapour and water vapour, in a water/ethyl-benzene molar ratio ranging from 5 to 15, preferably from 6 to 12, onto a first reactor in which a partial conversion of ethyl-benzene takes place. The reacted mixture leaving the first reactor is fed to a second reactor, after the temperature has been brought to the required value by means of a heat exchanger. The reaction mixture, in which the ethyl-benzene is converted for at least 50%, is cooled and condensed before being sent to the purification section. If required, at the outlet of the second reactor, it is possible to include a third reactor to increase the conversion of ethyl-benzene up to and over 70%.

The gases coming from the dehydrogenation reactors, leaving at a temperature ranging from 450 to 650° C., preferably from 550 to 610° C., are cooled in a series of exchangers which recover heat by preheating the feeding gases to the reaction section, up to a temperature ranging from 100 to 300° C., preferably from 120 to 180° C.; they then pass through ducts and/or equipment where, due to a series of water sprayers, they are washed and cooled to 30-100° C., preferably 55-70° C.; they are then condensed in the shell of a horizontal heat exchanger, in whose tubes a cooling fluid flows, for example water, in which condensation of a mixed type at reflux and equilibrium, takes place. In particular, the gases enter through the openings situated in the lower part of the shell, and move upwards, coming into contact with the exchanger tubes to which they transfer heat, as they begin to condense, the liquid formed by the condensation is refluxed by the action of the force of gravity, coming into contact with the rising gas which has not yet condensed. The following phenomena consequently take place contemporaneously in the shell of the exchanger: cooling, condensation and washing of the gases.

The washing of the gases and exchanger tubes on the part of the liquid which naturally downflows by gravity, ensures that the solid or viscous liquid particles are continuously washed out and removed from both the condenser and the incondensable gas which reaches the upper part of the mantle, where, due to a configuration obtained by means of longitudinal and transversal baffles, the gas is suitably cooled before being sucked by the compressors. The configuration described above has important advantages as it allows the condensation to be effected in a single apparatus and avoids the necessity of any type of cleaning for the whole operating duration.

The liquid mixture is sent to the second separation/purification section for the recovery of the vinyl-aromatic monomer. In particular, the liquid mixture which downflows into the lower part of the shell of the condenser is collected in specific areas and sent to a horizontal tank, situated below the condenser, where the two liquid phases, the phase rich in water and that rich in hydrocarbons, is separated by decanting. The aqueous phase is sent to treatment to remove the traces of hydrocarbons and solid particles, whereas the hydrocarbon phase, suitably filtered, is fed to the so-called separation/purification section for the recovery of the vinyl-aromatic monomer, for example, styrene.

The separation/purification section comprises at least one distillation column even if it is preferable to operate with three or four distillation columns connected in series with respect to the flow of monomer to be purified.

EXAMPLE

An example is provided, based on a comparison of industrial data in a production plant of styrene, which demonstrates the advantages that can be obtained with the improved condensing system, with condensation in the shell (called Improved Plant), compared with a traditional plant, in which the condensation takes place inside the tubes of two apparatuses arranged in series, the first cooled with air and the second with water (called Reference Plant).

The plant conditions are listed below.

The plant consists of a production section of ethyl-benzene to which ethylene and benzene are fed in the presence of a catalyst based on $AlCl_3$, at a pressure of about 0.5 MPa and a temperature of 150° C. The effluent from the reaction section is fed to a separation section, in which the catalyst based on $AlCl_3$ is separated and subsequently to a distillation section in which there are 3 tray columns. In the first, operating at about 0.6 MPa and a temperature at the head of 150° C., the non-reacted benzene is separated and is recycled to the reaction section; the bottom product is fed to a second column operating at 0.25 MPa and a temperature of 170° C., where the head product consists of ethyl-benzene which is sent to the subsequent dehydrogenation section, with a flow-rate of 40 t/h. The bottom product is fed to a third column operating at a pressure of 0.01 MPa and a temperature at the head of about 140° C. The head product, consisting of a mixture of polyethylated benzene compounds, prevalently diethyl-benzene, is recycled to the reaction section, whereas the bottom forms a by-product consisting of high-boiling products.

The dehydrogenation section, to which partly fresh and partly recycled ethyl-benzene is fed, consists of two adiabatic reactors situated in series containing a catalyst based on iron and potassium salts. The first reactor, to which ethyl-benzene is fed in gaseous form in the presence of water vapour, with flow-rates of 60 t/h (ethyl-benzene) and 100 t/h (water vapour) respectively, operates at an inlet temperature of about 610° C. and a pressure of about 0.085 MPa. The second reactor, on the other hand, operates at an inlet temperature of 630° C. and an inlet pressure of 0.05 MPa. The mixture leaving the $2^{nd}$ reactor at a temperature of 590° C. and a pressure of 0.04 MPa is cooled to about 150° C. in two exchangers situated in series, in which the heat is transferred, in the first exchanger, to the ethyl-benzene stream, in the second to the vapour, which are fed to the first reactor.

At the outlet of the last of these exchangers, the reaction gases are washed with about 50 t/h of water sprayed through a series of nozzles; the water thus injected partly vaporizes, cooling the gases to about 60° C. and remains partly in the liquid phase and refluxes onto the bottom of the tube. In this way, the gases are washed, before arriving at a tube bundle heat exchanger, called condenser, where most of them are condensed, whereas the incondensable part, rich in hydrogen, is cooled to about 30° C. and compressed in a suitable section. The part condensed at a pressure of 0.03 MPa and 55° C. flows by gravity into a horizontal tank situated below the tube bundle condenser; two phases are separated in the tank: the phase prevalently consisting of water, which is removed after removing the residual hydrocarbons, and the hydrocarbon phase, rich in styrene, but still containing non-reacted ethyl-benzene and lower concentrations of benzene, toluene and high-boiling products, called dehydrogenated mixture. The hydrocarbon stream, with a flow-rate of about 58 t/h, is pumped to the subsequent purification section consisting of four distillation columns. Benzene and toluene, forming the byproducts, are separated in the first column, where the dehydrogenated mixture is fed, at the head, at a pressure of 0.02 MPa and a temperature of approximately 55° C. The bottom product is fed to the second column, at a pressure of 0.03 MPa and a temperature of about 100° C.

A stream rich in ethyl-benzene is separated from the head of the second column, operating at 0.01 MPa and 65° C., which, after condensation, is pumped to the dehydrogenation section. The bottom product of the second column, at a temperature of about 90° C., is fed to the third column from whose head most of the styrene is obtained with a purity of over 99.7%, whereas the bottom product is fed to the fourth column, where further high-purity styrene is obtained at the head and a stream of high-boiling products, with a small amount of residual styrene, forming a waste by-product, is obtained at the bottom.

In the plant described above, the condenser of the effluent from the dehydrogenation section was originally of the type with condensation inside the tube and cooling fluid outside, followed by a smaller post-condenser. This condition is hereafter called "Reference Plant".

The condenser was then modified, as described above, and the condensation was effected inside the shell of a single exchanger in which the gases enter from the lower part of the shell and where the condensation takes place with a mixed reflux and equilibrium configuration. This situation is referred to below as "Improved Plant".

In the table below, various functioning parameters of the plant described above are compared, before and after effecting the modification, object of the present invention, with variations in the running time, after changing the dehydrogenation catalyst. The parameters compared are the following:

1. pressure at the condenser inlet, measured downstream of the dehydrogenation section of ethyl-benzene, step (d) before the inlet to the condensation/separation section, step (e), expressed in a relative form with respect to the initial figure, i.e. that which is measured with a completely clean plant and fresh catalyst;
2. plant capacity, measured by the flow-rate of the stream of styrene produced, expressed in a relative figure with respect to the initial form, i.e. that which is measured with a completely clean plant and fresh catalyst;
3. variation in the specific consumption of raw material, expressed as kg of ethyl-benzene necessary for producing 1 ton of styrene, obtained as a ratio between the flow-rate measurement of the stream leaving the production section of ethyl-benzene, measured in kg/h, and the flow-rate of the styrene stream, measured in t/h; the value in the table is expressed as the difference between the value per operating month considered and the initial value, i.e. that measured with a completely clean plant and fresh catalyst. For a better understanding of this parameter, it should be taken into account that it is influenced not only by the pressure, (the greater the pressure, the lower the selectivity and consequently the greater the specific consumption of ethyl-benzene), but also by the aging of the catalyst which jeopardizes the performances. The aging depends on the time the catalyst has spent under high temperature conditions and in contact with poisons deriving from the reagent stream.

TABLE

| Catalyst life months | Condenser pressure (%) | | Relative potentiality (%) | | Specific consumption variation (%) | |
|---|---|---|---|---|---|---|
| | Reference Plant | Improved Plant | Reference Plant | Improved Plant | Reference Plant | Improved Plant |
| 0 | 100 | 100 | 100 | 100 | 0 | 100 |
| 2 | 101 | 100 | 100 | 100 | 0.2 | 0.1 |
| 4 | 103 | 100 | 100 | 100 | 0.9 | 0.3 |
| 6 | 107 | 100 | 99 | 100 | 1.9 | 0.6 |
| 8 | 113 | 101 | 99 | 100 | 3.5 | 1.1 |
| 10 | 120 | 101 | 98 | 99 | 5.4 | 1.7 |
| 12 | 128 | 101 | 97 | 99 | 7.8 | 2.4 |
| 14 | 138 | 102 | 96 | 99 | 10.6 | 3.3 |
| 16 | 150 | 102 | 94 | 98 | 13.8 | 4.3 |
| 18 | 100(*) | 103 | 98(*) | 98 | 4.9(*) | 5.4 |
| 20 | 101 | 103 | 98 | 98 | 6.2 | 6.7 |
| 22 | 103 | 104 | 98 | 97 | 7.9 | 8.1 |
| 24 | 107 | 105 | 97 | 97 | 10 | 9.6 |
| 26 | 113 | 106 | 97 | 96 | 12.6 | 11.3 |
| 28 | 120 | 107 | 96 | 95 | 15.7 | 13.1 |
| 30 | 128 | 108 | 95 | 95 | 19.1 | 15.1 |
| 32 | 138 | 109 | 94 | 94 | 23 | 17.1 |
| 34 | 150 | 110 | 93 | 93 | 27.3 | 19.3 |

(*)The Reference Plant, with a traditional condenser, effects a shutdown for cleaning halfway through the useful life of the catalyst. The plant shutdown, which lasts about 10 days, implies a loss in production and additional costs, for both the shutdown operations and subsequent reactivation, and maintenance operations.

The invention claimed is:

1. An improved process for the production and purification of vinyl-aromatic monomers which comprises:
    a) feeding a stream consisting of an aromatic hydrocarbon together with a stream essentially consisting of a $C_2$-$C_3$ olefin to an alkylation section;
    b) feeding the reaction product coming from the alkylation section to a first separation section;
    c) discharging from the first separation section a first stream consisting of non-reacted aromatic hydrocarbon, which is recycled to the alkylation section, a second stream essentially consisting of a mono-alkylated aromatic hydrocarbon, a third stream essentially consisting of dialkylated aromatic hydrocarbons, sent to a transalkylation section, and a fourth stream essentially consisting of a mixture of polyalkylated aromatic hydrocarbons;
    d) feeding the second stream of step (c) to a dehydrogenation section;
    e) feeding the reaction product coming from the dehydrogenation section to a second separation/purification section, comprising at least one distillation column; and
    f) discharging a stream consisting of the vinyl-aromatic monomer with a purity of over 99.7% by weight, from the head of said at least one distillation column, wherein:
        after a first cooling with heat recovery, the gas leaving the dehydrogenation step, after washing with sprayed water, is fed and condensed in the shell of a tube bundle heat exchanger maintained vertical or horizontal, in whose tubes a cooling fluid flows;
        the gas feeding is effected from the lower part of the exchanger with the liquid deriving from the condensation which refluxes and leaves the exchanger, either totally or partially, still from the lower part of the shell and is sent to the second separation/purification section (e); and
        the possible gas and non-condensed substances leave the shell from the upper part of the exchanger.

2. The process according to claim 1, wherein the non-condensed gas Leaving the shell is sent to a further cooling step in a further heat exchanger, maintained vertical or horizontal, where the gas comes into contact with the tube bundle in the lower part of the exchanger, whereas the liquid deriving from the condensation of part of the gas, introduced specifically in the upper part of the shell, either totally or partially leaves the lower part of the shell and is sent to (e), the gas and non-condensed substances leaving the shell of the further exchanger from its upper part.

3. The process according to claim 2, wherein the
    gas non-condensed gas from the further exchanger is sucked by a compressor which increases its pressure and sends it for further cooling or condensation to the shell of one or more vertical or horizontal heat exchangers situated in series or in parallel, in whose tubes a cooling fluid flows, in which the gas comes into contact with the tube bundle in the lower part of the exchanger situated in series or in parallel, whereas the liquid deriving from the condensation of part of the gas introduced specifically in the upper part of the shell, either totally or partially leaves the lower part of the shell and is sent to (e), the gas and non-condensed substances leaving the shell of the exchanger situated in series or in parallel from its upper part.

4. The process according to claim 1, wherein the aromatic hydrocarbon fed to the alkylation section consists of refinery grade benzene, whereas the olefinic stream consists of refinery grade ethylene or propylene.

5. The process according to claim 4, wherein the olefinic stream consists of ethylene.

6. The process according to claim 1, wherein the aromatic and olefinic streams are fed to the alkylation section so as to have aromatic/olefinic molar ratios ranging from the group consisting of 1.8 to 50.

7. The process according to claim 1, wherein the alkylation reaction takes place in the presence of catalysts selected from aluminum trichloride, synthetic and natural porous crystalline solids based on silicon and aluminum, in which the silicon/aluminum atomic ratio ranges from 5/1 to 200/1 and synthetic zeolites of the ZSM group in which the silicon/aluminum atomic ratio ranges from 20/1 to 200/1.

8. The process according to claim 1, wherein the alkylation reaction is carried out at a temperature ranging from 50 to 450° C.

9. The process according to claim 5, wherein the catalyst consists of aluminum trichloride and the temperature ranges from 100 to 200° C.

10. The process according to claim 1, wherein the alkylation reaction is carried out at a pressure ranging from 0.3 to 6 MPa.

11. The process according to claim 1, wherein the aromatic stream leaving the alkylation reactor is fed to a separation system consisting of a series of at least three distillation columns for the recovery of the monoalkyl-substituted aromatic compound, to be sent to the dehydrogenation section.

12. The process according to claim 1, wherein the catalytic dehydrogenation reaction takes place in a fluid bed reactor, at a temperature ranging from 450 to 700° C. and a pressure ranging from 0.01 MPa to 0.3 MPa in the presence of a catalyst comprising one or more of the following metals: gallium, chromium, iron, tin, and manganese supported on alumina modified with 0.05-5% by weight of silica.

13. The process according to claim 1, wherein the catalytic dehydrogenation reaction takes place in a fixed bed reactor, at a temperature ranging from 500 to 700° C. and a pressure ranging from 0.02 MPa to 0.15 MPa in the presence of a catalyst based on iron oxide and potassium carbonate.

14. The process according to claim 1, wherein the second separation/purification section comprises three or four distillation columns connected in series with respect to the flow of monomer to be purified.

15. The process according to claim 1, wherein the heat exchanger is maintained horizontal and the cooling fluid is water.

* * * * *

UNITED STATES PATENT AND TRADEMARK OFFICE
CERTIFICATE OF CORRECTION

| | | |
|---|---|---|
| PATENT NO. | : 7,728,184 B2 | Page 1 of 1 |
| APPLICATION NO. | : 12/159162 | |
| DATED | : June 1, 2010 | |
| INVENTOR(S) | : Lucchini et al. | |

It is certified that error appears in the above-identified patent and that said Letters Patent is hereby corrected as shown below:

On the title page, Item (73), the Assignee should read:

-- (73) Assignee: Polimeri Europa S.p.A., San Donato Milanese (IT) --

Signed and Sealed this

Tenth Day of August, 2010

David J. Kappos
*Director of the United States Patent and Trademark Office*